United States Patent [19]
Hiebert

[11] Patent Number: 5,785,670
[45] Date of Patent: Jul. 28, 1998

US005785670A

[54] ADJUSTABLE CERVICAL COLLAR

[76] Inventor: Eugene Lloyd Hiebert, 3871 Concomly Dr., S.E., Salem, Oreg. 97306

[21] Appl. No.: 922,346

[22] Filed: Sep. 3, 1997

[51] Int. Cl.⁶ ..................................... A61F 5/00
[52] U.S. Cl. ........................... 602/18; 128/DIG. 23
[58] Field of Search ................. 602/17, 18; 128/DIG. 23

[56] References Cited

U.S. PATENT DOCUMENTS

| | | | |
|---|---|---|---|
| 2,818,063 | 12/1957 | Smith et al. | 602/18 |
| 3,512,523 | 5/1970 | Barnett | 602/18 |
| 3,696,810 | 10/1972 | Gaylord, Jr. | 602/18 |
| 3,916,884 | 11/1975 | Attenburrow | 602/18 |
| 4,401,111 | 8/1983 | Blackstone | 602/18 |
| 4,819,622 | 4/1989 | Taylor et al. | 602/18 |

OTHER PUBLICATIONS

Hermell Products, Inc. catalog, illustrating Four-Way Cervical Quickollar™ (cover and p. 16).

*Primary Examiner*—Linda C. Dvorak
*Attorney, Agent, or Firm*—Klarquist Sparkman Campbell Leigh & Whinston, LLP

[57] ABSTRACT

An adjustable cervical collar is fabricated from a one-half inch thick unitary neoprene member six inches wide by thirty-two inches long. The member includes a laterally extending center portion. It is scored on its inside surface to a depth of about three-eighths inch along the edges of the center portion to provide first and second portions that are foldable towards the outside surface of the center portion. The first foldable portion is wide enough to extend vertically above a patient's occiput and long enough to extend laterally to the patient's mastoid processes. The center portion is wide enough to support the patient's chin and to avoid excessive pressure against the patient's carotid arteries. Hook and loop fasteners attached to the inside and outside surfaces at opposite ends of the member permit the collar to be releasably fastened around the patient's neck. Folding one or the other or both of the foldable portions towards the outside surface permits the collar to adapt to four different neck sizes.

6 Claims, 2 Drawing Sheets

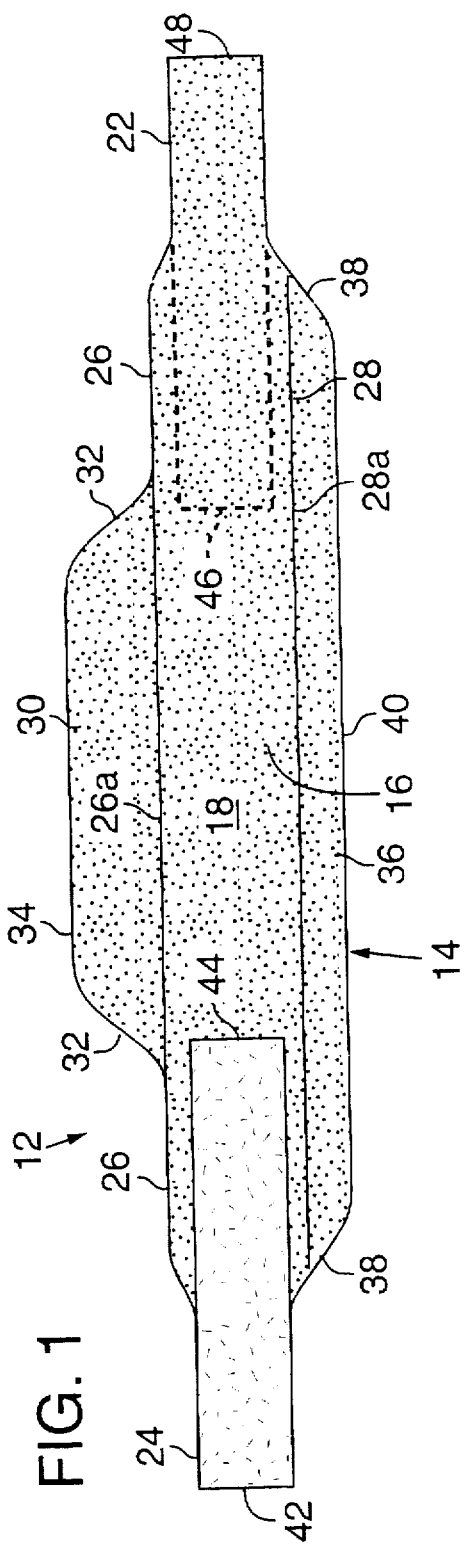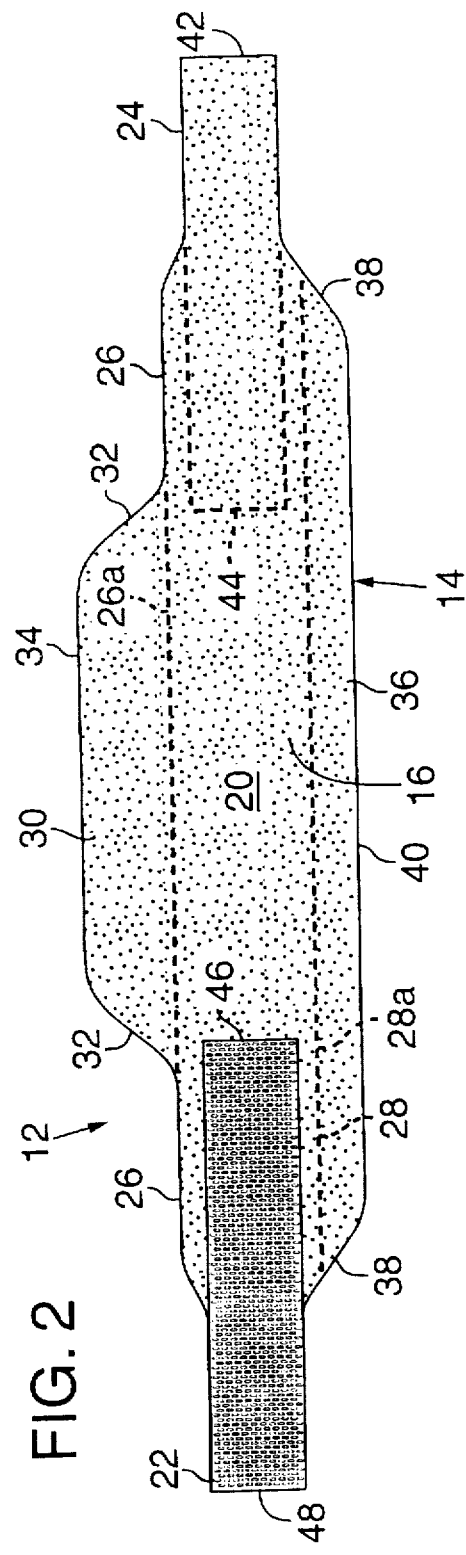

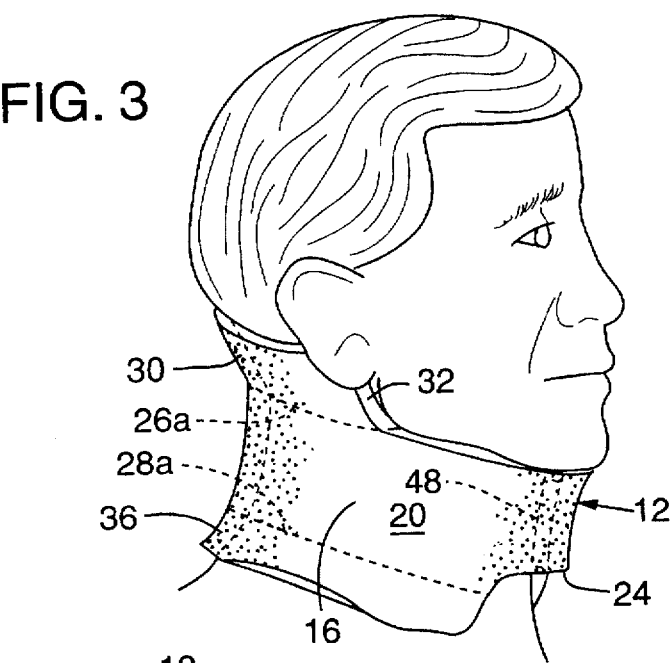
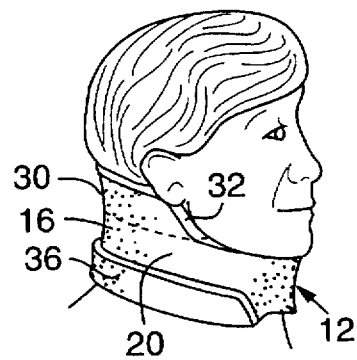
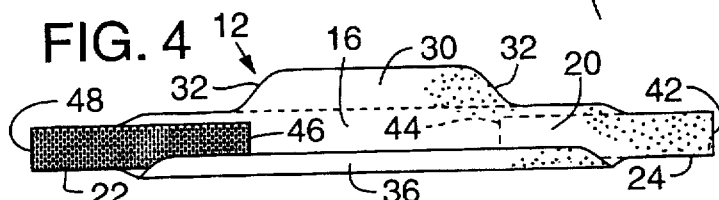
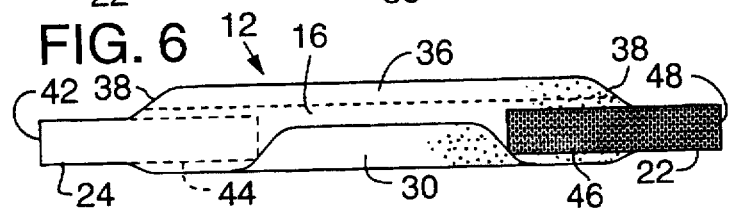
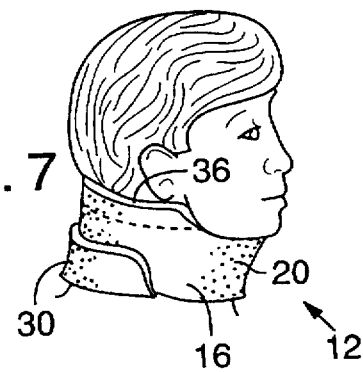
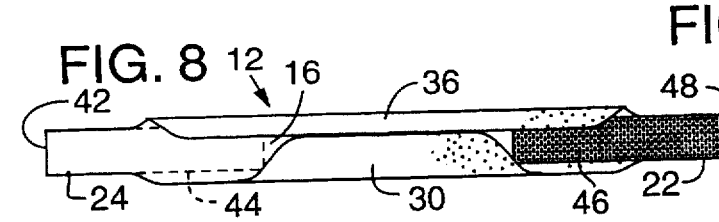
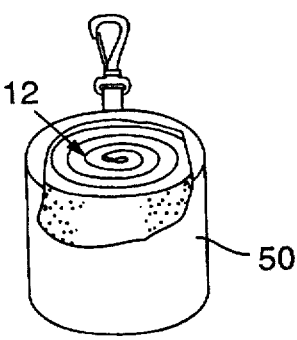
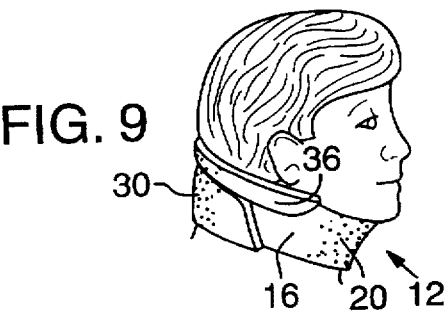

1

ADJUSTABLE CERVICAL COLLAR

FIELD OF THE INVENTION

This invention relates to cervical collars for immobilizing the cervical spine of an injured patient and, more particularly, to cervical collars adapted to be adjusted to fit different neck sizes.

BACKGROUND OF THE INVENTION

Cervical collars have long been used to immobilize injured patients. Generally, however, the collars have not been adjustable to fit different neck sizes. Instead, medical professionals have used collars of varying sizes as required to fit particular patients.

An adjustable cervical collar adapted to fit four different neck sizes has been manufactured and sold by Hermell Products, Inc., Bloomfield, Conn., as its 4-WAY QUICK-OLLAR™. The Hermell collar comprises a laterally extending center portion for wrapping around a patient's neck and two equal length foldable portions attached one to each of the lateral edges of the center portion. Hook and loop releasable fastening means, such as Velcro® fasteners, are attached to opposite ends of the center portion, one on the inside surface and the other on the outside surface thereof, so that the collar can be fastened securely around the patient's neck.

The center and foldable portions of the Hermell collar are made of separate one-quarter inch thick elastomeric members covered with and thereby joined together by an exterior plastic covering. The center portion of the Hermell collar is about two and one-eighth inches wide and about twenty-three and one-half inches long. The foldable portions are positioned generally centrally of the center portion and are trapezoidal in shape. The upper foldable portion is about one and three-eighths inches wide and fourteen and three-quarter inches long where it abuts the center portion. The lower foldable portion is about seven-eighths inch wide and also about fourteen and three-quarter inches long where it abuts the center portion.

The narrow widths of the Hermell foldable portions fail to provide adequate support when the collar is wrapped around the patient's neck, because the upper foldable portion is not wide enough to extend vertically above the patient's occiput and long enough to extend laterally to the patient's mastoid processes. The narrow width of the Hermell center portion fails to support the patient's chin in a neutral position and also tends to apply excessive pressure to the patient's carotid arteries. Also, the relatively stiff one-quarter inch thick elastomeric material from which the Hermell collar is made tends to bend acutely, and this also often results in the center portion applying excessive pressure to the patient's carotid arteries. The relatively stiff material from which the Hermell collar is made also prevents it from being rolled up compactly enough to be able to be placed in a carrying pouch.

It is thus the principal object of the present invention to provide an adjustable cervical collar that will provide improved lateral and rotational stability over that provided by previously known cervical collars.

It is a further object of the present invention to provide an adjustable cervical collar that will provide better support for the patient's chin with less pressure against the patient's carotid arteries than do previously known cervical collars.

It is a still further object of the present invention to provide an adjustable cervical collar that can be rolled up and placed in a compact carrying pouch.

It is a still further object of the present invention to provide an adjustable cervical collar as aforesaid that will be efficient and economical to manufacture.

SUMMARY OF THE INVENTION

My adjustable cervical collar achieves the foregoing and other objects. It comprises a laterally extending center portion for wrapping around a patient's neck. The center portion has an inside surface for placement against the patient's neck and an outside surface opposite thereto. The center portion has a width sufficient to support the patient's chin in a neutral position, and the width is also sufficient to avoid undue pressure against the patient's carotid arteries.

The collar further comprises a first foldable portion which abuts a first lateral edge of the center portion. The first foldable portion has a width sufficient to extend vertically above the patient's occiput and a length sufficient to extend laterally to the patient's mastoid processes. The first foldable portion is adapted optionally to be folded away from the patient's neck and toward the outside surface of the center portion.

The collar further comprises a second foldable portion which abuts the other lateral edge of the center portion. The second foldable portion is substantially longer but narrower than the first foldable portion. The second foldable portion is also adapted optionally to be folded away from the patient's neck and toward the outside surface of the center portion.

First releasable fastening means are attached to the inside surface of one end of the center portion and second releasable fastening means are attached to the outside surface of the other end of the center portion. Thus, fastening the first releasable fastening means to the second releasable fastening means fastens the collar securely around the patient's neck.

My cervical collar desirably comprises a unitary elastomeric member. The member is scored on the inside surface along the first and second lateral edges of the center portion, that is, along the lines of abutment of the first and second foldable portions with the center portion, whereby the first and second foldable portions are foldable along such scored first and second lateral edges (or lines of abutment) towards the outside surface of the center portion of the collar.

The elastomeric member desirably comprises a neoprene closed cell foam having a thickness of about one-half inch. The neoprene foam desirably has a compression deflection of between about two and five pounds per square inch, and a rebound average resilience of between about thirty-five and fifty percent, whereby the neoprene retains its rebound memory when the collar is rolled compactly into a roll and put in a pouch.

BRIEF DESCRIPTION OF THE DRAWINGS

FIG. 1 is a plan view showing the inside surface of my adjustable cervical collar in its completely unfolded condition.

FIG. 2 is a plan view showing the outside surface of the collar in its completely unfolded condition.

FIG. 3 is a view of the collar in the completely unfolded condition of FIGS. 1 and 2 shown wrapped around an adult patient's neck.

FIG. 4 is a plan view showing the outside surface of the collar with the second foldable portion folded up toward the outside surface of the center portion.

FIG. 5 is a view of the collar in its FIG. 4 condition shown wrapped around a teenage patient's neck.

FIG. 6 is a plan view of the outside surface of the collar with the collar turned upside down and with the first foldable portion folded up toward the outside surface of the center portion and the second foldable portion in its unfolded condition.

FIG. 7 is a view of the collar in its FIG. 6 condition shown wrapped around an adolescent patient's neck, that is, wrapped around the neck of a patient somewhat smaller than the patient shown in FIG. 5.

FIG. 8 is a plan view of the outside surface of the collar showing both first and second foldable portions folded up toward the outside surface of the center portion.

FIG. 9 is a view of the collar in its FIG. 8 condition shown wrapped around a child's neck.

FIG. 10 is a perspective view of the collar completely rolled up and inserted in a carrying pouch.

DESCRIPTION OF THE PREFERRED EMBODIMENT

Referring to the drawings, my adjustable cervical collar 12 is fabricated from a single unitary piece or member 14 of neoprene closed cell foam thirty-two inches long, six inches wide and one-half inch thick and having a center portion 16 that extends its full length. One surface 18 of the member 14 is adapted to be placed against the patient's neck. Surface 18 is denominated the inside surface. The opposite surface 20 is denominated the outside surface.

The center portion 16 is three inches wide over the major portion of its length, tapering in width to two inches at end portions 22, 24 that are each three and three-quarter inches long. The center portion 16 is further defined by scoring on its inside surface 18 along its lateral edges 26, 28, as shown. The inside surface 18 of member 14 is scored along lines 26a, 28a to a depth of three-eighths inch along each of the edges 26, 28 of the center portion 16.

A first foldable portion 30 two inches wide is disposed generally centrally of the center portion 16 and is defined at its inner edge by the scoring line 26a. The portion 30 is 14.3613 inches long at the scoring line 26a where it abuts the central portion 16 and tapers along forty-five degree transitional edges 32 to a length of 8.1387 inches at its exterior edge 34. The transition edges 32 are joined to the edge 26 of the center portion 16 and the exterior edge 34 of the foldable portion 30 by one and one-half inch radii. The portion 30 is foldable toward the outside surface 20 of the member 14 along the scored line 26a.

A second foldable portion 36 one inch wide is disposed generally centrally of the center portion 16 and is defined at its inner edge by the scoring line 28a. The portion 36 tapers along forty-five degree transitional edges 38 having one and one-half inch radii towards the end portions 22, 24 of the center portion 16. The exterior edge 40 of the portion 36 is positioned 6.7569 inches from the end surface 42 of the member 14. The portion 36 is foldable toward the outside surface 20 of the member 14 along the scored line 28a.

First releasable fastening means in the form of a ten inch long and two inch wide strip 44 of loop Velcro® is attached to the inside surface 18 of the center portion 16 commencing at the end 42 and extending inwardly. Second releasable fastening means in the form of a ten inch long and two inch wide strip 46 of hook Velcro® is attached to the outside surface 20 of the center portion 16 commencing at the opposite end 48 and extending inwardly. The collar 12 is fastened around the patient's neck by wrapping the collar around the neck and attaching the loop Velcro® strip 44 on the inside surface 18 of the center portion 16 to the hook Velcro® strip 46 on the outside surface 20 of the center portion 16.

Neoprene closed cell foam suitable for the member 14 is sold as Neoprene/EPT/SBR, stock Nos. 426N and 446N, by Industrial Rubber Company, Portland, Oreg. It has the following physical properties:

| | |
|---|---|
| Compression deflection, p.s.i. | 2–5 |
| Shore durometer, approximate average | 25–45 |
| Density, average, p.c.f. | 5–7 |
| Water absorption by weight, max. | 10% |
| Temperature range | |
| Low (flex without cracking) | –70° F.. |
| High continuous | 150° F.. |
| High intermittent | 200° F.. |
| Heat aging (7 days at 158° F..), | |
| Lineal shrinkage, max. | 10% |
| Tensile strength, p.s.i., min. | 30 |
| Elongation, % min. | 125 |
| Flammability-FMVSS #302, burn rate in inches/minute | 4 |
| Resilience, Bashore (% rebound average) (1/2" thickness @ 72° F..) | 35–50 |

Leaving the member 14 completely unfolded or folding one or the other or both of the foldable portions 30, 36 against the outside surface 20 of the member 14, permits my collar to accommodate four different neck sizes.

The collar is shown wrapped around the neck of an adult in FIG. 3. The upper edge 34 of the first foldable portion 30 is seen to extend above the patient's occiput and the transitional edges 32 of the portion 30 are seen to extend laterally to the patient's mastoid processes. The center portion 16 is seen to be wide enough to support the patient's chin in a neutral position, yet it avoids excessive pressure against the patient's carotid arteries, neither of which advantages is achievable by the Hermell collar.

The fact that the foldable portion 30 extends further up the patient's occiput vertically than does the Hermell collar, together with the fact that the portion 30 extends laterally to the patient's mastoid processes, result in much improved lateral and rotational stability than is achieved by the Hermell collar.

The thirty-two inch overall length of the collar 12 is long enough to accommodate a very large diameter neck; however, the fact that the length of the portion 30 is less than the length of the portion 36 results in an absence of interference of the transitional edges 32 with the patient's ears. The fact that each of the center and foldable portions 16, 30, 36 is wider than the corresponding portion of the Hermell collar creates greater overall stability.

Furthermore, the one-half inch thickness of my material provides greater stability than does the one-quarter inch thick Hermell collar. Also, my collar does not bend as acutely as does the Hermell collar and thus does not tend to press unduly against the patient's carotid arteries.

FIG. 4 illustrates the collar 12 with the second foldable portion 36 folded up toward the outside surface 20. FIG. 5 illustrates the collar 12 in its FIG. 4 configuration wrapped around the neck of a somewhat smaller patient, for example, a teenager. Again, the upper edge 34 of the portion 30 is wide enough to extend vertically above the patient's occiput; and the length is sufficient to extend laterally to the patient's mastoid processes, but not to interfere with the patient's ears.

FIG. 6 illustrates the collar 12 turned upside down, with the portion 30 folded up against the outside surface 20, but with the portion 36 in its unfolded configuration. FIG. 7 illustrates the collar 12 in its FIG. 6 configuration wrapped around the neck of a still smaller patient, for example, an adolescent patient.

FIG. 8 illustrates the collar 12 with both portions 30 and 36 folded up against the outside surface 20. FIG. 9 illustrates the collar 12 in its FIG. 8 configuration wrapped around the neck of an even smaller patient, for example, a small child.

FIG. 10 illustrates the collar 12 rolled into a compact roll, four inches by six inches in dimensions (the latter dimension being the width of the member 14), and inserted into a pouch 50. Despite the one-half inch thickness of the neoprene material comprising the member 14, the above cited compression deflection and resilience specifications enable the material to retain its rebound memory when unrolled. This is highly advantageous, because collars are often stored for long periods of time between uses.

I have compared the degree (percent) of immobilization provided by my collar with that provided by the Extrication Collar, the Hard Collar, the Philadelphia collar and, in greater detail with the Hermell Collar. I first compared my collar with the Extrication Collar, the Hard Collar and the Philadelphia Collar, comparing the data on my collar with data determined in the study reported in *The Journal of Trauma*, June 1983, by Podolsky et al. The results were determined by goniometry (an orthopedic protractor). They are as follows:

| | Percent Cervical Immobilization | | | |
|---|---|---|---|---|
| Type of Movement | Extrication Collar | Hard Collar | Philadelphia Collar | The Invention |
| Flexion | 26.1% | 27.7% | 32.2% | 70.5% |
| Extension | 14.3 | 26.7 | 42.9 | 69.7 |
| Lateral | 27.6 | 33.0 | 17.9 | 76.9 |
| Mean % Immobilization | 22.6 | 29.1 | 31.0 | 72.4 |
| The Collar of the Invention provided superior cervical immobilization by percentages of | | | | |
| | 49.8 | 43.3 | 41.4 | |

I then compared my collar in greater detail with the Hermell collar, in all four possible configurations. The data reflects the percent cervical immobilization achieved by each collar in the comparable configuration. Again, measurements were made by goniometry (the orthopedic protractor). The data is as follows:

I claim:

1. An adjustable cervical collar, comprising:

a laterally extending center portion for wrapping around a patient's neck, the center portion having an inside surface for placement against the patient's neck and an outside surface opposite thereto, the center portion having a width sufficient to support the patient's chin in a neutral position and avoid pressure against the patient's carotid arteries, the center portion having first and second lateral edges;

a first foldable portion attached to the first lateral edge of the center portion, the first foldable portion having a width sufficient to extend vertically above the patient's occiput and a length substantially shorter than the laterally extending center portion yet sufficient to extend laterally to the patient's mastoid processes, the first foldable portion being adapted optionally to be folded away from the patient's neck and toward the outside surface of the center portion;

a second foldable portion attached to the second lateral edge of the center portion, the second foldable portion being substantially longer and narrower than the first foldable portion, the second foldable portion being adapted to be folded away from the patient's neck and toward the outside surface of the center portion;

first releasable fastening means attached to the inside surface of one end of the center portion; and second releasable fastening means attached to the outside surface of the other end of the center portion, whereby fastening the first releasable fastening means to the second releasable fastening means fastens the collar securely around the patient's neck.

2. The cervical collar of claim 1, wherein the center portion and the first and second foldable portions comprise a unitary elastomeric member, the member being scored on the inside surface along the first and second lateral edges of the center portion, whereby the first and second foldable portions are foldable along the scored first and second lateral edges of the center portion.

3. The cervical collar of claim 2, wherein the elastomeric member comprises neoprene, the neoprene having a compression deflection of between about two and five pounds per square inch, the neoprene having a rebound average resilience of between about thirty-five and fifty percent, whereby the neoprene retains its rebound memory when the collar is rolled compactly into a roll.

4. The cervical collar of claim 2, wherein the elastomeric member comprises neoprene having a thickness of about one-half inch.

| | All Folds Open FIG. 1 Condition | | Second Foldable Portion Folded Up FIG. 4 Condition | | First Foldable Portion Folded Up FIG. 6 Condition | | First and Second Foldable Portions Folded Up FIG. 8 Condition | | Average Percent Immobilization | | Percent Better Immobilization by Invention |
|---|---|---|---|---|---|---|---|---|---|---|---|
| Position | Hermell | Invention | Hermell | Invention | Hermell | Invention | Hermell | Invention | Hermell | Invention | Collar |
| Flexion | 14.6% | 75.0% | 0% | 72.0% | 14.3% | 65.7% | 33.3% | 83.3% | 15.5% | 74.0% | 58.5% |
| Extension | 65.5% | 90.7% | 16.7% | 83.3% | 0% | 68.0% | 20.0% | 76.0% | 25.6% | 79.5% | 53.9% |
| Lateral | 38.9% | 82.0% | 33.3% | 84.5% | 19.5% | 75.0% | 40.6% | 84.5% | 33.1% | 81.5% | 48.4% |
| | | | | | Overall Improvement in Cervical Immobilization by Collar of the Invention | | | | | | 53.6% |

While a preferred embodiment of the adjustable cervical collar has been described in detail with reference to the drawings, it is understood that various changes and adaptations may be made in the collar without departing from the spirit and scope of the appended claims.

5. The cervical collar of claim 1, wherein the first releasable fastening means comprises loop fastening means and the second releasable fastening means comprises hook fastening means.

6. An adjustable cervical collar, comprising:

a unitary neoprene member having a thickness of about one-half inch, a compression deflection of between about two and five pounds per square inch, and a rebound average resilience of between about thirty-five and fifty percent, the member comprising:

a laterally extending center portion for wrapping around a patient's neck, the center portion having an inside surface for placement against the patient's neck and an outside surface opposite thereto, the center portion having a width sufficient to support the patient's chin in a neutral position and avoid pressure against the patient's carotid arteries, the center portion having first and second lateral edges, the member being scored to a depth of about three-eighths inch on the inside surface of the center portion along the first and second lateral edges thereof;

a first foldable portion attached to the first lateral edge of the center portion, the first foldable portion having a width sufficient to extend vertically above the patient's occiput and a length sufficient to extend laterally to the patient's mastoid processes, the first foldable portion being adapted to be folded along the first scored lateral edge of the center portion away from the patient's neck and toward the outside surface of the center portion;

a second foldable portion attached to the second lateral edge of the center portion, the second foldable portion being substantially longer than the first foldable portion, the second foldable portion being adapted to be folded along the second scored lateral edge of the center portion away from the patient's neck and toward the outside surface of the center portion;

loop releasable fastening means attached to the inside surface of one end of the center portion; and hook releasable fastening means attached to the outside surface of the other end of the center portion, whereby fastening the loop releasable fastening means to the hook releasable fastening means fastens the collar securely around the patient's neck.

* * * * *